United States Patent [19]

Cialone

[11] Patent Number: 4,521,193
[45] Date of Patent: Jun. 4, 1985

[54] METHOD AND KIT FOR CONSTRUCTING AN AESTHETIC AND FUNCTIONAL TEMPORARY DENTURE

[76] Inventor: Robert A. Cialone, 475 Shunpike Rd., Chatham, N.J. 07928

[21] Appl. No.: 297,468

[22] Filed: Aug. 28, 1981

[51] Int. Cl.³ ............................................. A61K 6/08
[52] U.S. Cl. ............................... 433/199; 260/998.11; 264/17; 264/18; 433/201; 433/213; 523/115
[58] Field of Search ............... 433/171, 199, 201, 213; 264/17, 18; 523/115; 260/998.11

[56] References Cited

U.S. PATENT DOCUMENTS 3,258,509  6/1966  Barnhart .............................. 264/17
3,567,806  3/1971  Dyal .................................... 264/18

Primary Examiner—Lorenzo B. Hayes
Attorney, Agent, or Firm—Millen & White

[57] ABSTRACT

A temporary denture can be rapidly produced while the denture user is in a dentist's office by filling a shell member with a molding composition. An impression of the outer surfaces only of a user's permanent denture is made in the molding compound and the tooth portions of the impression are then filled with a quick-cure, tooth colored curable acrylic composition, up to the gingival margin. Before the acrylic has cured, the remainder of the impression is covered with more of the curable acrylic composition which is colored pink until the gingival portion of the impression is covered by a thin layer of the acrylic. After setting, the thus-produced denture shell is removed from the mold, the surfaces thereof are then trimmed to correspond to the starting denture. The inner surface of the denture shell is then filled with soft curable denture liner and fitted in the user's mouth to form the temporary denture. A kit for making such temporary dentures comprises the molding shell; ingredients to form the tooth colored and pink acrylic polymer used to produce the denture shell and preferably also soft curable denture liner to form the inner surface of the finished denture.

10 Claims, 7 Drawing Figures

METHOD AND KIT FOR CONSTRUCTING AN AESTHETIC AND FUNCTIONAL TEMPORARY DENTURE

BACKGROUND OF THE INVENTION

The present invention relates to a temporary denture and a kit and method for producing the denture while the denture user is in the dentist's office.

When a denture user needs to have his denture repaired or relined, he often suffers the embarrassment of being seen in public without his teeth. There has not been developed a quick, effective and inexpensive way of producing a temporary denture which is aesthetically pleasing for use while a user's denture is being repaired.

U.S. Pat. No. 2,682,084 discloses a method of duplicating the teeth of a denture by taking an impression of the teeth portion of a user's denture and then filling the impression with a settable plastic tooth material. This process provides only for the making of the teeth of a denture and although expediting the manufacture of a permanent denture, fails to provide for an interim use temporary denture while the permanent denture is being made or repaired.

U.S. Pat. No. 3,465,440 discloses a temporary gum guard for use while the patient's denture is not in the mouth. The device of this patent however, is not designed to be aesthetically pleasing and functional, instead, it is merely designed to relieve the muscles of the mouth from strain while work is being done on the user's denture in the dentist's office, and not for general use during the time the user's permanent denture is being repaired.

SUMMARY OF THE INVENTION

It is therefore an object of the present invention to provide a temporary denture which comprises a single acrylic member having a first colored portion for the teeth portion and a second colored portion for the remainder of the denture body.

Another object of the present invention is to provide a method by which a temporary denture can be quickly produced in a shell containing a molding material which has been impressed with the permanent denture of a user.

Still another object of the present invention is to provide a kit for carrying out the method of the present invention for making the temporary denture of the present invention.

To accomplish these and other objects, the present invention includes a method for making a temporary denture and a kit for carrying out the method for making the temporary denture. The kit comprises a molding shell; impression molding material adapted to form an impression therein of a permanent denture; a curable polymerizable liquid acrylic composition adapted to form a denture when cured; first pigment adapted to color a portion of the curable acrylic composition tooth colored; and second pigment adapted to color another portion of the curable arylic composition gingiva colored. The molding shell is adapted to be filled with an amount of the molding material capable as supplied or after the addition of a plasticizing ingredient, e.g., water, of forming an impression or mold of the outer surfaces, i.e., the surfaces which do not contact the gingiva when worn, of a permanent denture when pressed into molding material. Before the impression sets, any damage to the permanent denture transferred to the impression, e.g., a crack or missing tooth, can be manually eliminated from the impression. Alternatively, the damage can be temporarily corrected, e.g., by inserting a temporary tooth in the missing area, before the impression is made. After the impression has been formed therein, the denture is removed, resulting in an exact duplication of the external surfaces of the user's denture. The molding material bearing the impression is then trimmed to the height of the denture flange. A curable polymerizable liquid acrylic composition rendered tooth colored by the addition of pigment is filled into the tooth portion of the impression, e.g., with an eye dropper. After the tooth portions are filled, the remaining surfaces of the impression are covered dropwise with a thin layer of polymerizable liquid acrylic composition which is colored pink, e.g., with an appropriate shade powder added thereto. The thickness of the layer, e.g., about 1 mm, is less than that of the corresponding portion of the permanent denture. After the acrylic shell has set, it is removed from the impression material and the margins are trimmed and outer surfaces are polished. The inside portion of the shell is then filled with a soft denture liner and placed in the patient's mouth so that the patient bites down and the mouth comes to rest at a height which was previously recorded. The denture liner is trimmed and shaped with a spatula and allowed to set.

There results a temporary denture which a user can wear while his permanent one is being relined or repaired; the temporary denture having been prepared in a short amount of time right in the dentist's office and from the original denture of the user.

Upon further study of the specification and appended claims, further objects and advantages of this invention will become apparent to those skilled in the art.

DETAILED DESCRIPTION OF THE INVENTION

Figure 6:
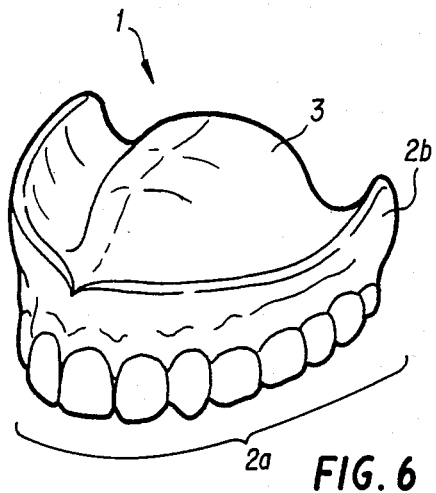
FIG. 6 is a perspective view of the finished one piece temporary denture of the invention.

The temporary denture 1 of the present invention shown in FIG. 6 consists of a one piece molded acrylic shell having a tooth portion 2a formed of an acrylic polymer which is tooth colored and a gingival portion 2b formed of a pink colored acrylic; and a liner portion 3 bonded to the upper surface of the gingival portion 2b of the shell.

To make this temporary denture, a kit is provided which includes a molding shell 7 adapted to receive an impression or molding material; a molding material, preferably an irreversible hydrocolloid such as, for example, an alginate, super gel, etc., in a form suitable for use as or conversion to a molding material; a rapidly curable material suitable to form a denture therefrom, e.g., a polymerizable acrylic prepolymer of methyl methacrylate, ethyl methacrylate, etc., presently available under trade names such as Lang's Jet Acrylic, Acralite, etc.; and means for forming cured polymers therefrom in two colors, e.g., two portions of the same acrylic prepolymer colored differently or preferably two coloring powders for adding to uncolored acrylic prepolymer, one to form a tooth color and one to form a gingiva color, preferably colors close to that of the permanent denture.

Lang's Jet Acrylic is packaged as a liquid acrylic and a powdered pigment which is added thereto. The powder comes in pink color as well as in other shades. The product produced therefrom is a composite filled resin which polymerizes in approximately 10 to 20 minutes after addition of the powder thereto.

Figure 7:
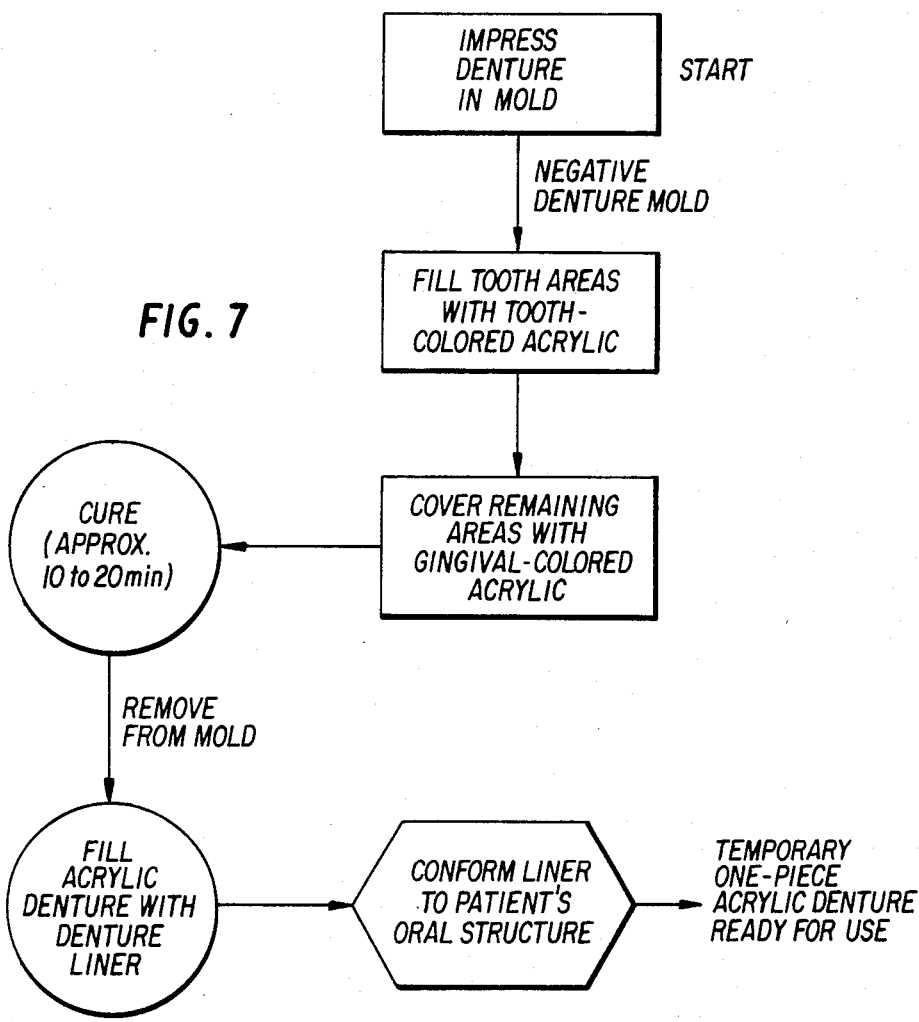
FIG. 7 is a flow chart of the steps of the process.

With reference to FIGS. 1 through 5, the process stages being shown therein, and FIG. 7 showing a flow chart of the process steps, the making of the temporary denture will now be described. The molding material is mixed with water to form a colloidal suspension which can be used to make a soft impressionable mold. The soft mold making material 9 is then filled into the shell 7 and shaped with a spatula so as to be compacted into the shell and made flat on the top surface thereof.

Figure 1:
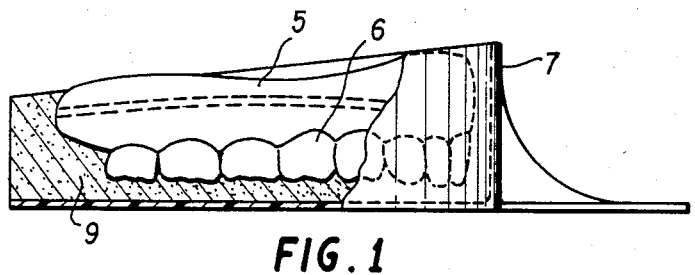
FIG. 1 is a side view, in partial section, of the molding shell filled with impression molding material and a permanent denture impressed in the latter.
Figure 2:
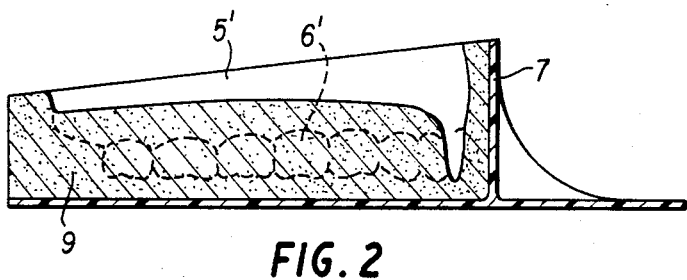
FIG. 2 is a view as in FIG. 1 with the permanent denture removed, and the impression molding material having been shaped to correspond to the outer surface of the patient's denture.
Figure 3:
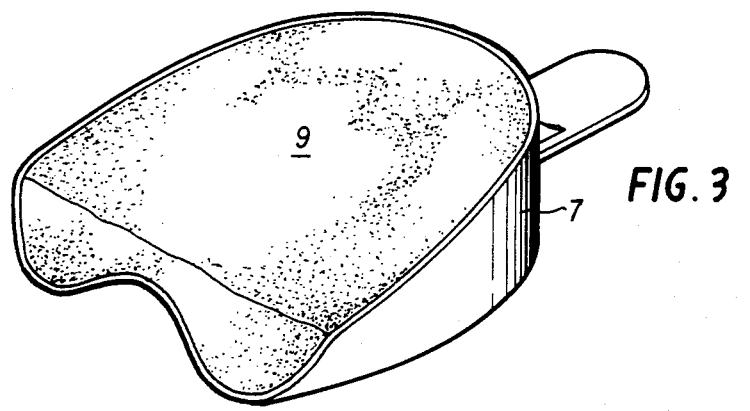
FIG. 3 is a perspective view of the shell filled with impression mold material prior to being impressed with the patient's permanent denture.
Figure 4:
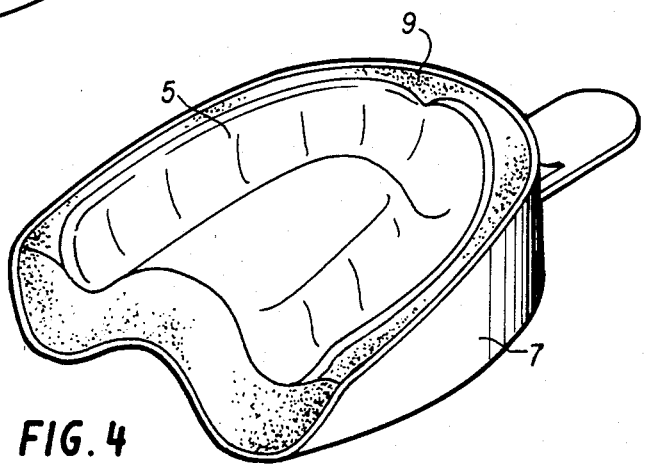
FIG. 4 is a perspective view of the shell of FIG. 3 with the patient's denture therein.
Figure 5:
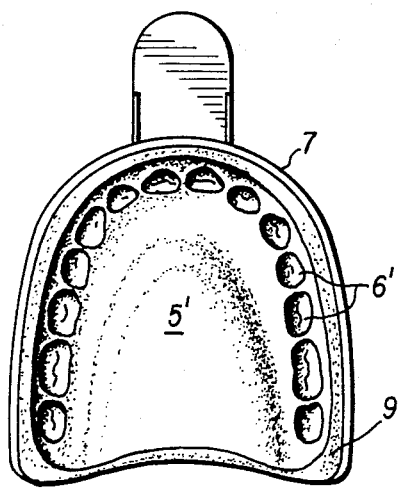
FIG. 5 is a top plan view of the already impressed molding material in the shell.

Subsequently, as shown in FIG. 1, the user's permanent denture 5 including tooth portion 6 is urged into the mold making material, thus forming an impression or mold of the outer portions or surfaces of the user's denture. At this point, damage to the permanent denture appearing in the impression, e.g., a missing tooth can be eliminated manually, e.g., by pressing an appropriately shaped tooth into the missing area. The, material 9 is allowed to set and then the denture is removed. Thus, there results an exact duplication 5' and 6' of the external surfaces of the user's denture. The impression material 9 is then trimmed to the level of the margin of the permanent denture flange.

To make the temporary denture, the polymerizable liquid acrylic composition having tooth colored powder mixed therein is placed in the tooth area of the impression mold until the material reaches the portion of the impression mold which corresponds to the gingival margin. This process is continued until all the tooth portions have been filled.

The remaining surface of the impression is covered with the acrylic which is colored pink by applying polymerizable liquid acrylic with a dropper to a small area, and immediately adding pink powder until all the liquid is absorbed. This process is continued until the entire surface is covered by a thin layer of pink colored acrylic having a thickness, e.g., on the order of approximately one millimeter, less than that of the corresponding portion of the permanent denture.

The curable acrylic is allowed to cure at least until the surface becomes dull, the time required being approximately 10 minutes. Once the surface is dull, the impression mold with the partially cured acrylic deposited thereon can be placed under hot water from the tap to accelerate the complete cure.

The resulting "acrylic shell" or single piece denture shell is removed from the impression material. The margins are trimmed and the outer surfaces are polished. Thus, the "acrylic shell" of the single piece temporary denture has been made and can now be prepared for use.

To finish the preparation of the temporary denture a soft denture liner is prepared, according to manufacturer's directions, and filled into the inside portion of the acrylic shell. Preferably, a denture liner such as is now made commercially available by Teledyne under the trade name of Soft-Oryl is used. Other denture liner's of the type now readily commercially available under trade names such as EZO, SNUG, etc. can also be used. The shell and liner combination is placed in the patient's mouth, and the patient is instructed to bite down until the upper and lower jaws are spaced at a distance corresponding to that determined earlier with the user wearing the permanent denture, e.g., by measuring the distance between reference points on the nose and on the chin, conveniently established by placing marks thereon.

When the denture liner material has set to a proper consistency, the denture is then removed and the liner material is smoothed and trimmed with a warm spatula around the margin of the flange of the denture. A temporary denture is thus prepared which the patient can wear while his permanent one is being relined or repaired, which functions like a permanent denture and is aesthetically pleasing so that the user will not have to undergo the embarrassment of being seen with a nonfunctional temporary denture or without any denture at all.

Additionally, as noted above if the denture from which the temporary denture is molded is missing a tooth or other part thereof, the missing part can be replaced before the impression is made or an appropriate correction in the impression in the impression can be made before the acrylic is applied thereto, so that the mold portion corresponding to the missing portion of the permanent denture will have a recess to be filled with acrylic at the time acrylic is added to make the temporary denture. Thus, even though the permanent denture has a missing portion, the resulting temporary denture will be structurally complete.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of making a temporary denture for a denture user, comprising the steps of:
   impressing the outer surfaces only of an existing permanent denture of the user into a settable molding composition to form a mold containing an impression of those surfaces;
   removing the denture from the mold;
   filling the tooth area only up to the gingival margin of the impression in molding composition with a quick cure tooth colored polymerizable acrylic composition;
   covering the remaining area of the impression in the mold with a thin layer of pink colored quick-cure polymerizable acrylic composition;
   allowing the acrylic composition to cure;
   removing the thus-formed acrylic denture shell from the mold;
   lining the inner surface of the thus-formed acrylic denture shell with a soft curable denture liner;

conforming the liner to the conformation of the contacting surfaces of the mouth; and
allowing said liner to set in the conformed shape, thereby forming the temporary denture.

2. A method as in claim 1, wherein said molding composition is an irreversible hydrocolloid.

3. A method as in claim 2, wherein said irreversible hydrocolloid is an alginate.

4. A method as in claim 1, comprising adding tooth colored pigment to clear polymerizable acrylic composition to make said tooth colored polymerizable acrylic composition, said pigment selected to be a color substantially corresponding to the tooth color of the permanent denture.

5. A method as in claim 1, wherein the denture has a missing portion and further comprising forming an additional impression in the mold corresponding substantially to the missing portion in the permanent denture.

6. A temporary denture which comprises a single acrylic member shell having first and second colored portions, said first colored portion corresponding to the teeth and having been made by filling the tooth portion of a molding composition mold, which has been impressed with the denture of a wearer, with a tooth colored polymerizable acrylic composition, said second portion corresponding to the remaining denture portion, being a pink colored portion and having been made by deposition of a layer of a pink color polymerizable acrylic composition on the remaining shell portions, said tooth colored polymerizable acrylic composition and pink color polymerizable acrylic composition having been allowed to dry into a single member to allow removal from the impressed shell, and said temporary denture further comprising a denture liner contained in said acrylic shell, said liner having been shaped to correspond to the mouth of the user for allowing said user to wear said acrylic shell in the mouth.

7. A substitute denture as in claim 6, wherein said layer of pink color polymerizable acrylic composition is about 1 mm thick.

8. A substitute denture as in claim 6, wherein the color of said tooth colored polymerizable acrylic composition substantially corresponds to the color of the tooth portion of the user's permanent denture.

9. A kit for making a temporary denture comprising:
a molding composition adapted for making a soft molding material for forming an impression therein from a permanent denture;
a generally denture shaped shell adapted for having the molding composition material packed thereinto;
a quick-cure polymerizable acrylic;
a tooth colored powder for being added to a portion of said polymerizable acrylic for coloring said portion of polymerizable acrylic;
a pink powder for being added to another portion of said polymerizable acrylic for coloring said another portion of polymerizable acrylic; and
a soft denture liner for filling into the inside portion of the temporary denture acrylic shell made from said different portions of colored polymerizable acrylic for adapting the temporary denture shell to a patient's mouth for wearing by the user.

10. A kit as in claim 9, further comprising dispenser for depositing said polymerizable acrylic dropwise.

* * * * *